US008681941B2

(12) United States Patent
Bernhardt et al.

(10) Patent No.: US 8,681,941 B2
(45) Date of Patent: Mar. 25, 2014

(54) METHOD FOR VISUALIZING A PATIENT DOSE, COMPUTER PROGRAM PRODUCT AND X-RAY APPARATUS

(75) Inventors: Philipp Bernhardt, Forchheim (DE); Martin Knierim, Erlangen (DE)

(73) Assignee: Siemens Aktiengesellschaft, München (DE)

(*) Notice: Subject to any disclaimer, the term of this patent is extended or adjusted under 35 U.S.C. 154(b) by 327 days.

(21) Appl. No.: 13/166,999

(22) Filed: Jun. 23, 2011

(65) Prior Publication Data

US 2011/0317815 A1    Dec. 29, 2011

(30) Foreign Application Priority Data

Jun. 29, 2010  (DE) .......................... 10 2010 025 512

(51) Int. Cl.
*H05G 1/64* (2006.01)
(52) U.S. Cl.
USPC ............................... 378/98.5; 378/98; 378/97

(58) Field of Classification Search
USPC .......................... 378/62, 95, 96, 97, 98, 98.5
See application file for complete search history.

(56) References Cited

U.S. PATENT DOCUMENTS

| | | | |
|---|---|---|---|
| 6,934,362 B2 * | 8/2005 | Scheuering | 378/108 |
| 7,103,139 B2 | 9/2006 | Nagaoka et al. | |
| 7,801,273 B2 * | 9/2010 | Hoornaert et al. | 378/97 |
| 2010/0290591 A1 * | 11/2010 | Spahn | 378/98.5 |

* cited by examiner

Primary Examiner — Courtney Thomas

(57) ABSTRACT

A method for visualizing a dose of X-ray radiation applied to a surface of a patient in a defined time period by an X-ray apparatus is proposed. The X-ray apparatus is adjustable to different angular positions. A model of the surface of the patient is provided. The dose of X-ray radiation applied to the surface of the patient in the defined time period is calculated. The model and the calculated dose on the model is visualized. The visualization of the model and the calculated dose on the model is effected in an angular position coupled to the angular position in which the X-ray apparatus is currently disposed.

18 Claims, 2 Drawing Sheets

METHOD FOR VISUALIZING A PATIENT DOSE, COMPUTER PROGRAM PRODUCT AND X-RAY APPARATUS

CROSS REFERENCE TO RELATED APPLICATIONS

This application claims priority of German application No. 10 2010 025 512.2 filed Jun. 29, 2010, which is incorporated by reference herein in its entirety.

FIELD OF THE INVENTION

The present invention relates to a method for visualizing the dose of X-ray radiation applied to a surface of a patient in a defined time period by means of an X-ray apparatus that can be adjusted to different angular positions, to a computer program product or computer program for a visualization control device of an X-ray apparatus for performing the method, to a data medium having a computer program product stored thereon, and to an X-ray apparatus by means of which the method can be performed.

BACKGROUND OF THE INVENTION

In X-ray based medical imaging a patient is exposed to a radiation risk. It is imperative to minimize this risk without constraints being imposed on the medically necessary requirements.

C-arm systems are used very frequently for medical diagnostics and in the present case said systems are to serve as an example of X-ray apparatuses which can be adjusted to different angular positions during the image acquisition. Systems of this kind are characterized in that radiation can be passed through the patient in any direction without the patient having to be repositioned. This is of great advantage in particular in angiography, since vessels can be assessed and treated better when they can be examined from different sides.

In X-ray diagnostic systems there is generally not only the stochastic radiation risk but also in addition a deterministic risk which denotes the danger that the skin on the radiation input side will be burned if the dose is too high. With regard to the deterministic risks, in contrast to the stochastic risk, it is possible in most cases to specify dose limit values below which deterministic radiation damage can be almost totally ruled out. For this reason physicians will usually proceed in such a way that during a diagnosis or, as the case may be, a treatment they will change the angulation, i.e. the angular position, of the X-ray apparatus every once in a while for radiation protection reasons in order to distribute the entry radiation exposure over a greater area of the body. In order to support the physicians in this endeavor programs have been developed which determine the surface dose on a location-dependent basis with the aid of models and report said dose back to the physician. In this case the patient surface currently being irradiated is determined from the angular position of the X-ray apparatus and the so-called collimation, i.e. the area or, as the case may be, field which is radiated onto the patient by the X-ray source. The doses that have accrued on said areas over a specific time period are subsequently aggregated and displayed or visualized on a display. Since the treating or diagnosing physician is occupied with numerous medical tasks, it represents an additional onerous task for him/her if he/she then also has to rotate the model with the dose displayed thereon so that the angular position of the model corresponds to the angular position of the X-ray apparatus.

U.S. Pat. No. 7,103,139 B2 discloses a method according to the preamble of claim 1 for displaying the dose of X-ray radiation applied to a surface of a patient in a defined time period by means of an X-ray apparatus which can be set to different angular positions.

SUMMARY OF THE INVENTION

Accordingly, the object underlying the present invention is to develop the method described in the introduction in such a way that the application of the method is improved or made easier for the physician. A further object underlying the invention is to provide a corresponding computer program or computer program product which can be stored on a data medium and which implements the method according to the invention. Yet another object underlying the present invention is to disclose an X-ray apparatus by means of which the method according to the invention can be performed.

These objects are achieved by a method, a computer program product, and an X-ray apparatus as claimed in the independent claims. Advantageous developments of the invention are the subject matter of the dependent claims.

The approach adopted in the method according to the invention is that a model of the surface of the patient is provided. The expression "provide" can signify in the present context that for example a new model of the surface of the patient is created, an existing model of said type is retrieved for example from a memory and used, or an existing model is modified and used. The X-ray radiation dose that is or has been applied to the surface of the patient in a defined time period is then calculated. The defined time period over which the dose is determined typically encompasses a time interval ranging from approximately 20 minutes up to eight hours. However, other time intervals can also be relevant in individual cases. Measuring the dose is important in particular because the skin damage in the form of burns caused as a result of the application of X-ray radiation appears only after about ten to 30 days. Because of this great time delay between X-ray radiation being applied and the damage manifesting itself it is consequently no longer possible to react to damage that has occurred. The dose can also be calculated already prior to providing the model or simultaneously therewith. Finally the model is visualized in precisely that angular position in which the X-ray apparatus is also currently located, with the calculated dose likewise being visualized on the model. By coupling the angular position of the X-ray apparatus on the one hand and the model on the other it is ensured that there is no necessity for the physician to perform any additional actions in order to be able to view the model in the angular position suitable for him/her. Thus, for example, he/she can adjust the X-ray apparatus to the angular position or angulation in which he/she plans to carry out the irradiation. In said angular position he/she then sees instantly whether the dose aggregated thus far is already so great that it is advisable to perform the irradiation using a different angulation, or whether the dose delivered in the planned angular position allows the intended irradiation. Administering treatment is therefore greatly simplified for the treating physician by means of the method according to the invention. Susceptibility to errors can also be reduced considerably because it cannot happen that the previous radiation exposure on a surface in the first angular position is displayed while the following irradiation in a second angular position which is different from the first angular position is performed.

The present invention is based on the fact that a physician does not require a complete overview in respect of the applied dose or the dose to be applied, but only the current exposure on the currently irradiated surface, as well as the impact on the environment, which are available as possible alternatives. It is therefore ensured by means of the invention that precisely the relevant information is presented in an automatic manner. Should it transpire that a new irradiation angulation is necessary due to the preceding radiation, this position can be found in a simple and optimal manner by moving the X-ray apparatus, since the visualization of the model with the dose radiated onto the surface—also referred to as the dose map—automatically moves in concert.

It is self-evident that the method according to the invention is generally computer-implemented and consequently is performed in an automated manner and requires no interaction with the user.

According to a preferred embodiment variant of the inventive method, changing the angular position of the X-ray apparatus also causes the visualization of the angular position of the model as well as the dose visualized on the model to move in synchronism therewith. For the physician this means that he/she only needs to change the angular position or angulation of the X-ray apparatus and the angulation or angular position of the surface of the model will be automatically aligned accordingly. Thus, even when the angular position of the X-ray apparatus is changed, the physician is not required to perform any additional activity in order to be able to correct or adjust the surface-related dose visualization as well.

A particularly graphic visualization of the dose exposure on the surface, and one that is easily recognizable and distinguishable for a physician, is produced when the calculated dose is visualized as a texture.

The ability to distinguish different dose exposures on the surface is further increased if a color coding scheme is resorted to for the local strength distribution.

The visualized dose is reproduced or an impression thereof given particularly effectively when the model or, as the case may be, its surface is represented three-dimensionally. In this case the spatial assignment can be further improved if the model simulates a schematic or realistic representation of the body of the patient or at least a part thereof.

For the physician, administering the treatment or applying the method is simplified even further if not just the X-ray radiation applied thus far to the surface of the patient is visualized on the model, but also the area which is currently being irradiated by the X-ray apparatus in its present angular position on the surface of the patient or which would be irradiated in the event that the X-ray apparatus is currently not in operation. This area, which is also referred to as a collimation and represents a bundle of rays which is allowed through, i.e. radiated onto the patient, by a corresponding diaphragm of the X-ray apparatus, gives the physician an additional visual indication of where the planned or currently running X-ray irradiation impinges onto the surface of the patient. It is particularly preferred in this situation if the area is represented centrally on the model. In other words the area is therefore not displayed at the upper or side edge of the model, but precisely or at least substantially in its center. It can mean an additional alleviation for the physician if the area is always displayed at the same position on the display device—a computer monitor, for example. That is to say that the area is located at the same position on the monitor even when the model is rotated. Thus, the irradiated area is used as it were as a fixed point or fixed area under which the model rotates.

The method according to the invention can be employed in a particularly favorable manner with a C-arm X-ray apparatus.

An advantageous development of the method according to the invention consists in providing the possibility of decoupling the angular position of the model—i.e. its visualization—from the angular position of the X-ray apparatus in order to enable the model or, as the case may be, its visualization to be rotated independently of the angular position of the X-ray apparatus. By means of such an "override" option of intervening in the method to the extent that the angular positions of the model and of the X-ray apparatus can be chosen independently of one another, it is possible for the user—at least briefly—to be able to rotate the visualization of the model without on that account having to rotate the entire X-ray apparatus in terms of its angular position. In certain situations this may save time, because usually the X-ray apparatus cannot be moved as quickly as a visualization on a monitor.

In this case it is of advantage if the coupling of the angular position of the visualization of the model to the current angular position of the X-ray apparatus is effected automatically when or even before the X-ray apparatus can emit its radiation, i.e. when an irradiation is triggered. It can be advantageous here if the X-ray apparatus even cannot start to operate until it has been ensured that the user has registered the fact that the new coupling has taken place, for example in that the user gives a new command for actuating the X-ray apparatus. In this way it can be ensured that an actuation of the X-ray apparatus cannot be initiated by mistake on the basis of an incorrect angular representation of the model, i.e. an incorrect assignment of the angular position of the model to the angular position of the X-ray apparatus. If necessary the X-ray apparatus can output a warning signal in the form of an alarm tone or a visual signal if an irradiation is initiated with the angular positions being decoupled from one another. At any event it must be possible to ensure that a treating physician can produce an X-ray photography without delay at any time—for example during an intervention—in order to obtain information concerning the condition of the patient immediately from the X-ray image in an emergency situation.

It can be of advantage if, after the angular positions have been decoupled from one another, the user can cause—for example by operating a switch or with the aid of a computer mouse—the X-ray apparatus to move or pivot automatically into the angular position in which he/she is currently viewing the model. This function can produce a time saving for the user and increase the degree of precision, since the most recently chosen angular position for viewing the model no longer needs to be changed, because the angular position of the X-ray apparatus is aligned to the current angular position for viewing the model, and not vice versa.

It can also be advantageous to make a prediction for the area which is being irradiated by the X-ray apparatus in its current angular position on the surface of the patient and indicate how much longer the area can continue to be irradiated as a function of the already transmitted maximum local dose in the area until a specific dose threshold value is reached. Preferably also included in addition to the selected X-ray parameters in order to make said prediction is the thickness of the patient under the area that is necessary for determining the minimum strength of the X-ray radiation required for achieving a good or at least adequate image visualization.

The object underlying the invention is also achieved by means of a computer program or computer program product as claimed in claim 15 by means of which a visualization control device of an X-ray apparatus can be operated in order to perform one of the aforesaid methods according to the invention. The object underlying the invention is furthermore achieved by means of a data medium as claimed in claim 16 on which an aforesaid computer program product is stored.

The object underlying the invention is finally achieved by means of an X-ray apparatus as claimed in claim 17 which has a pivotable X-ray emitter and an associated X-ray detector, a calculation device for calculating the dose of X-ray radiation applied to a surface of a patient in a defined time period by means of the X-ray apparatus, a display device for visualizing the calculated dose, and a visualization control device for controlling the display device in accordance with one of the aforesaid methods. An X-ray apparatus of said kind offers the same advantages as have been described already in connection with the method as claimed in claim 1 or one of the claims dependent thereon.

A preferred embodiment variant of the X-ray apparatus according to the invention is characterized in that a decoupling device such as for example a corresponding key or a corresponding button for releasing the coupling of the angular position of the visualization of the model to the angular position of the X-ray apparatus is provided so that the visualization of the model can be rotated independently of the X-ray apparatus. This may produce a time saving for the user, since the visualization of the surface of the model with the dose represented thereon on a display device is usually quicker to deal with than the angular adjustment of the X-ray apparatus.

For safety reasons there is provided in an advantageous development of the X-ray apparatus according to the invention a coupling device which automatically recouples the angular positions of the visualization of the model and of the X-ray apparatus when the X-ray apparatus is to be actuated. If the arrangement has been realized in such a way that the actuation of the X-ray apparatus will only be possible when it has been ensured that the user is aware of the recoupling of the angular positions and therefore in all probability has also checked whether the irradiation is actually to be started at the right angular position, this ensures a considerable degree of operational safety.

BRIEF DESCRIPTION OF THE DRAWINGS

Further advantages, features and specifics of the invention will emerge from the following detailed description of advantageous embodiment variants of the invention with reference to the drawings, in which.

DETAILED DESCRIPTION OF THE INVENTION

Figure 1:
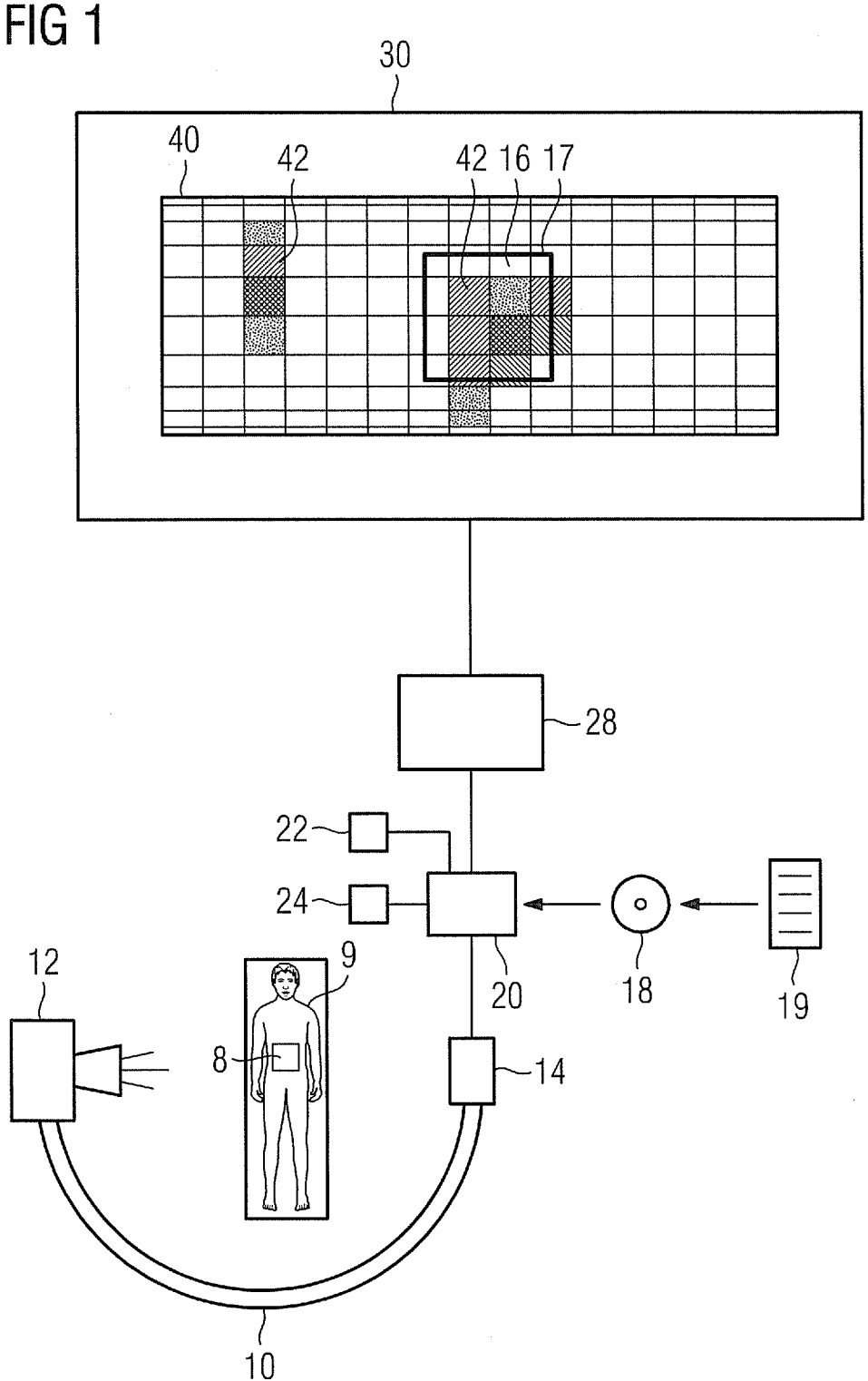
FIG. 1 shows an advantageous embodiment variant of the X-ray apparatus according to the invention, wherein the dose is visualized on a simple model.

FIG. 1 schematically shows an X-ray apparatus 10 embodied as a C-arm device comprising an X-ray emitter 12 that can be pivoted in terms of its angular position and an associated X-ray detector 14 permanently connected to the X-ray emitter 12. A patient 9 can be arranged between the X-ray emitter 12 and the X-ray detector 14 for the purpose of diagnosis or therapy. Connected to the X-ray detector 14 is a calculation device 20, in the form of a computer for example, which can calculate the dose 42 that is radiated by the X-ray apparatus 10 onto a surface 8 of the patient 9 within a specific time period. The calculation device 20 is connected to a display device 30 such as a computer monitor for example on which it can display the calculated dose 42. The calculation device 20 is also connected to a visualization control device 28 which controls the display device 30 (this point will be dealt with in more detail later). The visualization control device 28 can also be a separate computer or microprocessor or else be included in the calculation device 20.

The visualization of the X-ray radiation applied to the surface 8 of the patient 9 during a specific time period is then performed in the following way: The visualization control device 28 provides a model 40 of the surface 8 of the patient 9 by retrieving an already existing model from a memory, by creating a new model or by modifying a known model. In this example a first shape of the model 40 is a cylinder. On said model 40, an area 16 in the center is indicated by means of a square 17, said area 16 being irradiated by the X-ray emitter 12 as soon as the latter is actuated. The dose exposure aggregated thus far is displayed on the cylindrical model 40, which constitutes a simple representation of the body of the patient 9, in the form of a texture, which in this case is composed of different grayscale values, at the respective position by the visualization control device 28 on the display device 30. It is clear that the dose 42 has previously been calculated by the calculation device 20 over the time period of the examination and is updated each time the X-ray apparatus is actuated (radiation initiation). The update can be performed online, i.e. the visualization control device 28 is controlled by means of a computer program 19 which can be stored for example on a CD 18 as an example of a data medium. In this case the visualization control device 28 is controlled in such a way that it does not represent the model 40 independently of the X-ray apparatus 10, but visualizes the model 40 in exactly the same angular position in which the X-ray apparatus 10 is also disposed. This means, in other words, that if the X-ray emitter 12 and the associated X-ray detector 14 are rotated or pivoted, the model 40 is also rotated or pivoted in the same way. The arrangement is realized in such a way that the area 16 always remains at the same position on the display device 30, whereas the model 40 as it were revolves under the area 16. Should the collimation and hence the size of the irradiated area be changed, the size of the area 16 naturally also changes accordingly.

It is particularly advantageous if the dose 42 is visualized by means of colors which can be used as coding for the strength of the dose at the respective localities. Since the model is three-dimensional, the spatial assignment is made easier for the user.

Thus, as soon as the X-ray apparatus 10 is pivoted together with the X-ray emitter 12 and the X-ray detector 14, the angular position of the model 40 and the dose 42 visualized on the model 40 are also pivoted or moved in synchronism.

A decoupling device 22 can be provided for example in the form of a pushbutton or rotary knob by means of which the coupling of the angular position of the visualization of the model 40 to the angular position of the X-ray apparatus 10 can be released. Following actuation of the decoupling device 22 the visualization of the model 40 can therefore be rotated independently of the X-ray apparatus in order for example to be able to consider other angular positions and consequently other surfaces 8 of the patient 9 prior to an irradiation and verify whether they are suitable for an irradiation. Rotating the model 40 independently of the X-ray apparatus 10 may in this case produce a time saving, since rotating the model 40 can be executed faster than pivoting the X-ray apparatus 10.

The angular positions of the visualization of the model 40 on the one hand and of the X-ray apparatus 10 on the other hand can be recoupled for example by reactuation of the decoupling device 22. It is, however, preferred that a coupling device 24 be provided which detects the decoupling effected by means of the decoupling device 22 and automatically performs a coupling of the angular position of the visualization of the model to the current angular position of the X-ray apparatus when (or even before) the X-ray apparatus 10 is reactuated. By this means the coupling device 24 can ensure that firstly it will be possible to produce an X-ray photograph at any time. Secondly it is ensured that at least in the future the actual situation of the irradiation of the surface 8 of the patient 9 by means of the X-ray apparatus 10 is visualized on the model 40. Optionally the coupling device 24 can alternatively inhibit an actuation of the X-ray apparatus 10 until such time as a user has indicated—for example by a new actuation of the decoupling device 22—that he/she has taken note of the now recoupled angular position and would actually like to perform an irradiation in this angular position. Operational safety can be considerably improved in this way, because by this means an irradiation of the patient 9 in an actually undesired angular position can be prevented.

Figure 2:
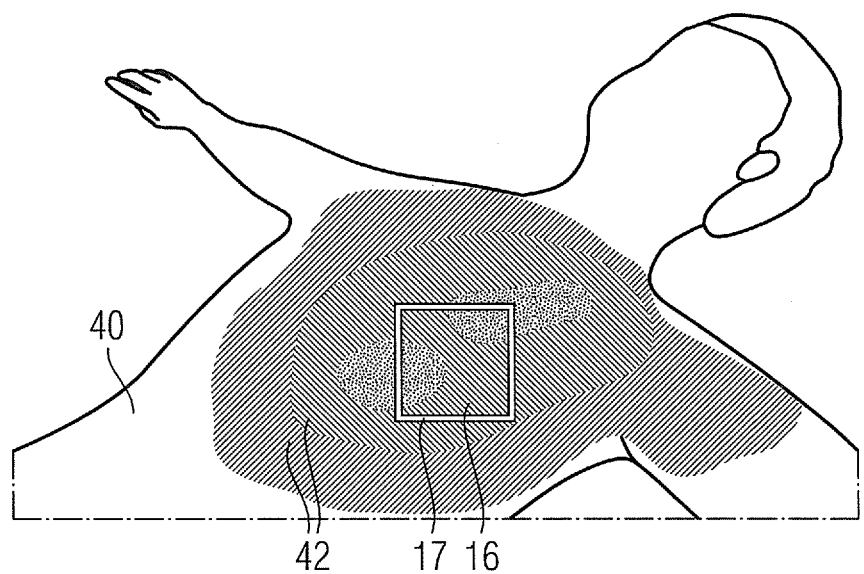
FIG. 2 shows a further type of visualization of the model.

A further possibility of visualizing the model 40 is shown in FIG. 2. In this case the model 40 is embodied as a relatively realistic mapping of a human body and consequently simplifies the spatial assignment of the irradiation between model and reality even further. Exactly as in the case of the model according to FIG. 1, the area 16 is represented by a square 17—in this case indicated by white lines. The dose 42 radiated in the past is visualized on the surface of the model 40, the local distribution of the strength of the dose 42 over the body being particularly clearly recognizable in this case. In this embodiment of the model 40 too the area 16 remains at the same position when the X-ray apparatus 10 is pivoted, although the model 40 is rotated accordingly. According to this visualization the area 16 is not in the center of the model 40. It is therefore self-evidently possible that the environment of the area 16 in which the dose 42 is to be indicated on the model 40 can be changed as necessary by a user. This can be effected for example by zooming, i.e. by setting a smaller or larger magnification of the visualization. Zooming of this kind would therefore not even require the decoupling device 22 to be actuated. A merely translational displacement of the visualization of the model 40 likewise requires no actuation of the decoupling device 22 as long as the angular position of the visualization of the model 40 and of the X-ray apparatus 10 is not changed. It is clear that a rectangle or another shape can also be used for the area 16 instead of a square 17, depending on how this is predefined by the X-ray apparatus 10 or is beneficial for a treatment.

It shall be understood that the method according to the invention and the X-ray apparatus according to the invention are closely linked to one another and that features of the invention that have been described as method-related aspects may also be essential to the X-ray apparatus. This can also apply conversely for features described with reference to the X-ray apparatus which may also be relevant in respect of the method.

It goes without saying that features described with reference to individual embodiments may also be implemented in other embodiments or embodiment variants, except when this is expressly described otherwise or is automatically precluded for technical reasons.

The invention claimed is:

1. A method for visualizing a dose of an X-ray radiation applied to a surface of a patient in a time period by an X-ray apparatus, comprising:
    providing a model of the surface of the patient;
    calculating the dose of the X-ray radiation applied to the surface of the patient in the defined time period; and
    visualizing the model and the calculated dose on the model, wherein the visualization is effected in an angular position coupled to a current angular position in which the X-ray apparatus is currently disposed.

2. The method as claimed in claim 1, wherein the visualization is moved synchronously along with a movement of the X-ray apparatus.

3. The method as claimed in claim 1, wherein the calculated dose is visualized as a texture.

4. The method as claimed in claim 1, wherein a local strength distribution of the dose is visualized by a color coding scheme.

5. The method as claimed in claim 1, wherein the model is three-dimensional.

6. The method as claimed in claim 1, wherein the model comprises a schematic representation of a part of the body of the patient.

7. The method as claimed in claim 1, wherein an area irradiated by the X-ray apparatus in the current angular position on the surface of the patient is visualized on the model in addition to the dose.

8. The method as claimed in claim 7, wherein the visualization of the model moves in the area as a function of movements of the X-ray apparatus.

9. The method as claimed in claim 7, wherein the area is represented centrally on the model.

10. The method as claimed in claim 7, wherein a time period for how long the area needs to be irradiated is indicated as a function of a maximum local dose in the area until a defined dose threshold value to be reached.

11. The method as claimed in claim 1, wherein the X-ray apparatus is a C-arm X-ray apparatus.

12. The method as claimed in claim 1, wherein the angular position of the visualization is released with the current angular position of the X-ray apparatus so that the visualization of the model is rotated independently with the X-ray apparatus.

13. The method as claimed in claim 11, wherein the X-ray apparatus is automatically adjusted to an angular position in which the model is currently being viewed after the release.

14. The method as claimed in claim 12, wherein the angular position of the visualization of the model is automatically coupled again to the current angular position of the X-ray when or before the X-ray apparatus starts to emit the X-ray radiation.

15. A computer program product executable in a control device of an X-ray apparatus for visualizing a dose of an X-ray radiation applied to a surface of a patient in a time period by the X-ray apparatus, the computer program product when executed in the control device executing steps comprising:
    providing a model of the surface of the patient;
    calculating the dose of the X-ray radiation applied to the surface of the patient in the defined time period; and
    visualizing the model and the calculated dose on the model, wherein the visualization is effected in an angular position coupled to a current angular position in which the X-ray apparatus is currently disposed.

16. An X-ray apparatus, comprising:
    a pivotable X-ray emitter;
    an X-ray detector;
    a calculation device for:
        providing a model of the surface of the patient, and
        calculating a dose of an X-ray radiation applied to a surface of a patient in a time period by the X-ray apparatus;
    a display device for visualizing the model and the calculated dose on the model; and
    a control device for controlling the visualization to be effected in an angular position coupled to a current angular position in which the X-ray apparatus is currently disposed.

17. The X-ray apparatus as claimed in claim 16, further comprising a decoupling device for releasing the coupling of the angular position of the visualization with the current angular position of the X-ray apparatus so that the visualization of the model can be rotated independently with the X-ray apparatus.

18. The X-ray apparatus as claimed in claim 17, further comprising a coupling device for automatically recoupling the angular position of the visualization to the current angular position of the X-ray apparatus when or before the X-ray apparatus starts to emit the X-ray radiation.

* * * * *